United States Patent [19]

Wright et al.

[11] Patent Number: 4,585,542

[45] Date of Patent: * Apr. 29, 1986

[54] THERMAL PROTECTION METHOD FOR ELECTROANALYTICAL CELL AND AMPEROMETRIC PROBE

[75] Inventors: Harry D. Wright, Collonge-Bellerive; John M. Hale, Meinier; Eugen Weber, Hinwil, all of Switzerland

[73] Assignee: Orbisphere Corporation Wilmington, Succursale de Collonge-Bellerive, Collonge-Bellerive, Switzerland

[*] Notice: The portion of the term of this patent subsequent to May 21, 2002 has been disclaimed.

[21] Appl. No.: 691,519

[22] Filed: Jan. 14, 1985

Related U.S. Application Data

[63] Continuation of Ser. No. 345,536, Feb. 3, 1982, Pat. No. 4,518,477.

[51] Int. Cl.[4] .......................................... G01N 27/46
[52] U.S. Cl. .................................. 204/415; 204/241; 204/408; 204/409; 165/47; 165/177
[58] Field of Search ............... 204/239, 241, 408, 409, 204/415; 165/47, 177

[56] References Cited

U.S. PATENT DOCUMENTS

| | | | |
|---|---|---|---|
| 3,127,200 | 3/1964 | Sayag | 165/177 |
| 3,510,421 | 5/1970 | Gealt | 204/415 |
| 4,003,705 | 1/1977 | Buzza et al. | 204/415 |
| 4,024,042 | 5/1977 | Enfors et al. | 204/415 |
| 4,096,047 | 6/1978 | Hale et al. | 204/400 |
| 4,169,387 | 10/1979 | Kpempl | 165/47 |
| 4,185,620 | 1/1980 | Hagihara | 204/415 |
| 4,206,018 | 6/1980 | Kreisel et al. | 204/241 |
| 4,248,712 | 2/1981 | Bauermeister | 204/415 |
| 4,276,926 | 7/1981 | Evangelow | 165/47 |
| 4,401,547 | 8/1983 | Schinkmann et al. | 204/415 |
| 4,432,366 | 2/1984 | Margules | 204/415 |
| 4,455,213 | 6/1984 | Neti et al. | 204/415 |
| 4,518,477 | 5/1985 | Wright et al. | 204/415 |

FOREIGN PATENT DOCUMENTS 2013895A  8/1979  United Kingdom .................. 204/415

*Primary Examiner*—T. Tung
*Attorney, Agent, or Firm*—Werner W. Kleeman

[57] ABSTRACT

A method of thermal protection of a membrane-enclosed amperometric cell of the type comprising an electrolyte within an electrolyte space containing electrodes and enclosed by a semi-permeable membrane which defines a sensor face; heat exchange within said cell is effected for controlled heat compensation of the electrolyte when the sensor face is exposed to temperatures outside of the operative temperature range of the cell.

A membrane-enclosed amperometric probe having an elongated body provided with a sensor face at one end of the body and with electrical electrode connections extending through the probe body; the body includes at least two elongated fluid-passing conduits which are not in fluid communication with the electrolyte space and which extend in axial direction through the body from a first region near the one body end to a second region near the other body end; the conduits have mutually communicating ends in the first region and separate fluid-feeding ends in the second region so as to permit passing a fluid through the probe body.

4 Claims, 8 Drawing Figures

THERMAL PROTECTION METHOD FOR ELECTROANALYTICAL CELL AND AMPEROMETRIC PROBE

CROSS-REFERENCE TO RELATED APPLICATIONS

This application is a continuation application of our commonly assigned, copending U.S. patent application Ser. No. 06/345,536, filed Feb. 3, 1982, now U.S. Pat. No. 4,518,477, granted May 21, 1985.

This application generally relates to subject matter disclosed in our commonly assigned U.S. application Ser. No. 773,163 filed Mar. 1, 1977, issued as U.S. Pat. No. 4,096,047 on June 20, 1978, as well as to subject matter disclosed in our commonly assigned U.S. application Ser. No. 164,291, filed June 30, 1980, now U.S. Pat. No. 4,325,797, granted Apr. 20, 1982, and the copending divisional application Ser. No. 06/319,708, filed Nov. 9, 1981, now U.S. Pat. No. 4,372,021, granted Feb. 8, 1983.

BACKGROUND OF THE INVENTION (a) Field of the Invention

This invention relates generally to the art of amperometric measurement and amperometric measuring devices of the type used for quantitative electrochemical analysis methods where the concentration of an electroactive species such as oxygen dissolved in or admixed with a fluid is to be measured or monitored; more particularly, this invention relates to an improved method of thermally protecting an amperometric cell or probe which is temporarily subjected to temperatures outside of the operative cell temperature range, such as in heat sterilization.

The invention further comprises an improved probe provided for passage of a fluid, such as a cooling liquid, through said probe.

(b) Description of the Prior Art

Electrochemical cells of the type used for quantitative electrochemical analysis are well known in the art and generally include a working or sensing electrode having a defined or electroanalytically effective surface, a counter electrode, an optional guard electrode, an electrolyte in contact with the electrodes and a membrane that is substantially impermeable to the electrolyte but is permeable to the electroactive species of interest and defines the sensor face in terms of a barrier between the electrolyte space, notably the electrolyte film on top of the sensing electrode, and the ambient medium that contains the electroactive species.

For amperometric analytical operation, the working electrode of such a cell arrangement is polarized by a constant DC voltage to furnish a current whose steady state magnitude is proportional to the activity of the electroactive species of interest. Cells of this type and their operation and uses are discussed in detail in the following illustrative U.S. Pat. Nos. 2,913,386, 3,071,530, 3,223,608, 3,227,643, 3,372,103, 3,406,109, 3,429,796, 3,515,658, 3,622,488 and 4,096,047 as well as in British Published Application No. 2,013,895.

Structural and operational data of such prior art cells can be found in the literature, particularly in the Monography by Fatt, Irving, "Polarographic Oxygen Sensors", CRC-Press, Inc., USA, 1976, incorporated herein by reference.

The first mentioned U.S. Pat. No. 2,913,386 to Leland E. Clark considered as the pioneering patent in this art already teaches a semi-permeable membrane that restrains the electrolyte and the terms "membrane-covered" or "membrane-enclosed" are being used generally to refer to such electroanalytical devices, e.g. as "membrane-covered polarographic detectors".

As the term "polarography" has also been used for techniques based on the dropping mercury electrode and operating either in a voltametric or galvanic mode, the term "membrane-enclosed amperometric cell" or MEAC is used herein to refer to electroanalytical probes such as the "Clark Cell" and modifications thereof including those that use guard electrodes and various devices to improve operation, reliability, sensitivity and maintenance.

Because of the high sensitivity, e.g. for routine determinations of dissolved oxygen in water in the ppm to ppb range, MEAC-type oxygen probes are of interest in various types of industrial microbiological processes including enzymatic or fermentative methods, where reliable monitoring of the oxygen content is of paramount interest.

Microbiological methods require that the equipment which is exposed to a biologically active and, hence, biodegradable medium must be sterilizable; heat sterilization, such as exposure to temperatures above 100° C., e.g. pressurized steam of 120° C., for periods in the range of minutes or hours is a generally preferred method for heat sterilization of processing equipment, such as fermenters, feeding pipes and other devices that have come, or will come, in contact with a process stream containing biologically active matter.

As a consequence, oxygen probes for use in such processes should be heat-sterilizable but because MEACs include temperature sensitive constituents, one of which is the electrolyte, this presents substantial problems. Thus, when a MEAC typically designed for operation at a temperature between 0° C. and 40° C. is exposed to 120° C. steam, the following damaging effects may occur:

expansion of the volume of the electrolyte relative to the space available, creating internal pressures which tend to stretch the membrane;

shrinkage, softening and creeping of structural parts of the probe producing permanent dimensional changes;

stresses of differential expansion of disparate materials, leading to permanent damage of structural parts;

recrystallization or phase changes of the membrane material causing permeability changes which, even if but temporary, can cause measurement errors for a time;

enhanced solvent power and corrosiveness of electrolyte at elevated temperatures causing attack on structural parts.

A conventional way around these problems is to use a MEAC that can be taken out of the system to be monitored when the latter is heat-sterilized and to effect sterilization by other than thermal treatment. As actual measurement is neither required nor normally possible during heat-sterilization periods, this is feasible per se but requires a substantial procedural effort, aside from the problems of a reliable sterilizing treatment for the probe that does not introduce uncontrolled sterilant residues into the system which is to be monitored.

Cooling of the MEAC would seem to provide another way to resolve heat-sterilization problems; yet, probe cooling implies that exposed parts of the probe do not reach sterilization conditions and remain contaminated.

Finally, use of a non-aqueous electrolyte solvent having a boiling point above 120° C. and a low vapor pressure at that temperature would seem to offer another way around some of the difficulties set forth above but as the requirements for such a solvent are quite demanding, no practicable solution appears feasible.

The operative temperature range of a MEAC containing an aqueous electrolyte, i.e. the temperatures of an ambient medium which do not damage the MEAC or modify its sensitivity, may be broadened somewhat by electrolyte additives, such as thickeners, and such additives are in fact being used in prior art heat-sterilizable sensors which, in addition to electrolyte additives, provide for mechanically compensating the thermal expansion of the electrolyte during in-line heat-sterilization. The disadvantages of such a system are decreased sensitivity and less reliability, prolonged stabilization periods, frequent exchange of membrane and electrolyte, and relatively complicated structures and maintenance requirements.

OBJECTS AND SUMMARY OF THE INVENTION

Accordingly, it is a main object of the invention to provide for a method of thermally protecting a MEAC or probe having an operative temperature range typical for aqueous electrolytes when the MEAC is to be kept in-line during heat-sterilization periods so that the sensor face, at least, of the MEAC is exposed to temperatures substantially above the operative range of the MEAC.

Another object of the invention is to provide for a MEAC-type probe suitable for in-line use in an environment that is subject to periodic heat-sterilization treatment.

A further object of the invention is to provide for a MEAC-type probe that permits passing of a fluid into and out of the cell structure.

Yet another object of the invention is to provide for a MEAC-type probe having a shield against thermal shock.

Further objects will become apparent as the specification proceeds.

It has been found according to a first general method embodiment of the invention that the above objects and further advantages will be achieved when effecting a heat exchange within a MEAC for controlled heat compensation of the aqueous electrolyte within the MEAC, generally by heat exchange with the electrolyte, when exposed to temperatures substantially outside of the normal operative temperature range.

According to a first general apparatus embodiment the invention provides for a MEAC probe that includes, in its body, at least two elongated fluid-passing conduits which are not in fluid communication with an electrolyte space and which extend in axial direction through said body from a first region near one end of the body to a second region near the other body end; the conduits have mutually communicating ends in the first region and separate fluid-feeding ends in the second region and permit passing of a fluid through the probe body.

The heat exchange with the aqueous electrolyte is effected by controlled heat compensation and this includes operation in a manner that does not prevent sterilization of those external or "exposed" portions of the probe that have, or are intended to, come into contact with biologically active medium that is to be monitored.

Surprisingly, it has been found according to the invention that controlled heat compensation of the electrolyte by direct or indirect heat exchange therewith provides for sterilizing conditions at the exposed probe portions including the sensor face without adverse effects on the MEAC when operating according to the invention. While not wishing to be bound to a specific theory, it may be assumed that the heat capacity of the aqueous electrolyte and its relatively poor heat conductivity is the main reason that controlled electrolyte heat compensation according to the invention is capable of resolving the problems encountered with conventional sterilizable MEAC probes including those operating with expansion control.

BRIEF DESCRIPTION OF THE PREFERRED EMBODIMENTS

Preferably, the heat exchange step according to the inventive method includes passing a stream of a heat transfer fluid, preferably a liquid, through the cell for indirect or direct heat exchange with the electrolyte. In direct heat exchange, the electrolyte may be used as the heat transfer fluid; for economy and convenience of operation an indirect heat exchange within the MEAC is used for controlled heat compensation of the electrolyte, and a heat transfer fluid, such as water, is passed through the cell to contact a heat conductive cell member, such as an electrode, which in turn contacts the electrolyte space and thus is in a heat conducting connection with the electrolyte therein.

It is preferred for many purposes of the invention to effect the indirect heat exchange with the electrolyte by passing the heat transfer fluid through a substantially annular and confined fluid-passing channel or chamber sealed from the electrolyte space but in heat exchange or heat conducting contact therewith by a heat conducting cell member, preferably the outermost electrode of a coaxial electrode arrangement.

Such coaxial electrode arrangements include a central electrode, e.g. the sensing electrode or cathode, and at least one peripheral electrode, e.g. the counter electrode or anode, that extend around the central electrode. Optionally, a guard electrode may be included in the coaxial electrode arrangement between the central electrode and the outermost or peripheral electrode, and an electrical insulator is provided between any two adjacent electrodes at least. Such coaxial arrangements are known per se, i.e. without fluid circulation means, and are disclosed, for example, in our above-mentioned U.S. Pat. No. 4,096,047 and in British Published Application No. 2,013,895, both of which are incorporated herein by way of reference.

Preferred coaxial electrode arrangements with or without a guard electrode include a well portion or electrolyte reservoir in the electrolyte space, and the confined annular fluid-passing channel or chamber should be in heat exchange contact with such well portion. Passing of heat transfer fluid through the annular channel or chamber preferably is effected by fluid-passing conduits or conduit means which are not in fluid communication with the electrolyte space and which may be formed by grooves or the like recesses at the interface of a pair of coaxial tubular cell members explained in more detail below. Preferably, such a tubular pair is used to provide for a thermal shield that extends through a major portion, at least, of the probe body within the probe jacket, and a thermal insulator, such as an air gap, between jacket and shield can be provided to assure that the shield has no substantial cooling effect upon those outer jacket portions that are intended to be exposed to heat sterilization.

DEFINITION OF TERMS

The phrase "controlled heat compensation of the electrolyte" as used herein refers to the condition of maintaining the electrolyte at temperature conditions that will not damage the cell or modify its sensitivity while the exposed external parts of the probe are subject to temperature conditions that without such heat compensation would damage the cell, or modify its sensitivity. Such compensation is controlled by the heat flux; for example, when heat-sterilizing (120° C.) a MEAC according to the invention, a typical heat flux for controlled heat compensation of the electrolyte when the MEAC is heat-sterilized may be in the order of 10 to 500 Kilojoules per hour and such heat flux, in turn, can be controlled by the passing rate of the heat transfer fluid, the temperature condition and type of heat transfer fluid used and other parameters that are known per se in the heat exchange art. As an illustrative example when using tap water as heat transfer fluid in a probe according to the invention, a rate of 2 to 20 liters per hour may be sufficient for adequate heat flux control.

The term "operative temperature" of a MEAC is intended to refer to that temperature range within which a given MEAC can be operated without adverse effects as to cell structure and sensitivity. It will be understood that maintaining the sensitive inner portions and notably the aqueous electrolyte of a MEAC at an operative temperature during heat-sterilization does not imply actual operation (oxygen sensing) of the cell during heat-sterilization. In fact, while such continued operation is possible with the inventive method and apparatus, amperometric values measured in an ambient medium under heat-sterilization conditions with a probe in which the electrolyte is at a substantially lower temperature are not normally significant.

The terms "heat conductive" and "thermally conductive" are used interchangeably herein and refer to materials and connections having a heat conductivity, expressed in Joule.sec$^{-1}$.m$^{-1}$.K$^{-1}$, of above 0.5, preferably at least about 1.5; a preferred heat conductivity range is between 3.5 and 5.0 or more.

Correspondingly, the terms "thermally insulated" or "thermally insulating" refer to materials and connections having a heat conductivity of substantially below 0.5, e.g. below 0.05 or lower when expressed in terms of the above units.

BRIEF DESCRIPTION OF THE DRAWINGS

The present invention is illustrated by way of example and not limitation in the figures of the accompanying drawings, in which.

DETAILED DESCRIPTION OF THE PREFERRED EMBODIMENTS

FIGS. 1A, 1B and 2A, 2B of the drawings illustrate a schematic example of an amperometric electroanalytical cell including heat exchange means; the example is shown merely for the purpose of explaining the workings of the method according to the invention.

Figure 1A:
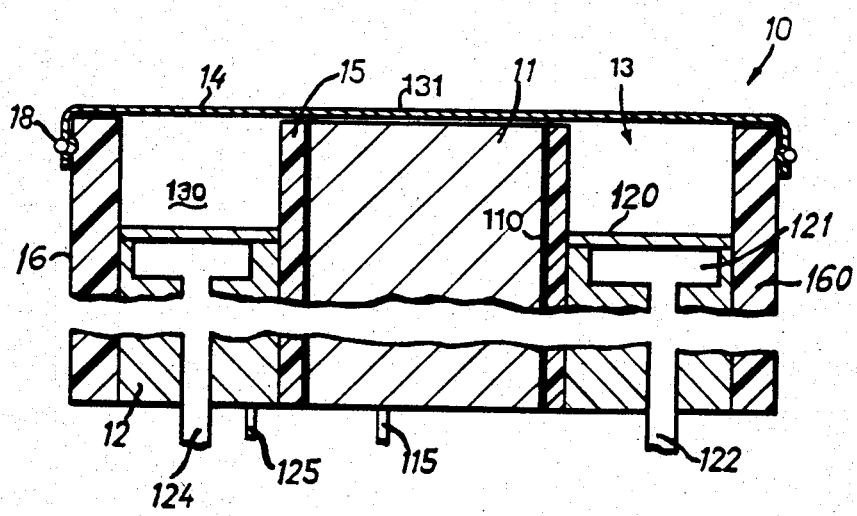
FIG. 1A is a cross-sectional view illustrating the operation of the inventive method with reference to schematic example of an amperometric electroanalytical cell including an internal heat exchange means and shown in a diagrammatic and fragmented presentation.

The diagrammatic sectional view of cell 10 shown in FIG. 1A includes a working electrode or cathode 11, a counter electrode or anode 12, an electrical insulator 15 between the electrodes 11, 12 and an electrically insulating jacket 16 around electrode 12.

The electrolyte-containing space 13 is in contact with both electrodes 11, 12 by means of an electrolyte well or reservoir 130 that contacts anode 12 and an electrolyte film 131 covering the surface of cathode 11. The electrolyte-containing space 13 is enclosed by membrane 14 held on jacket 16 by a membrane-holding member 18. Each electrode 11, 12 has a separate electrical outlet or lead 115, 125 for connection with a measuring circuit or instrument (not shown).

Membrane 14, e.g. a thin film of polytetrafluoro ethylene, is impermeable to the electrolyte in space 13 but permeable to an electroactive species in an ambient medium that is in contact with the outer surface of membrane 14.

The frontal sensor face on the elongated body of cell 10 is defined essentially by the outer surface of membrane 14 above electrolyte film 131 on top of electrode 11 and the reaction of electroactive species will occur at the electrolyte-exposed surface of cathode 11. In order to prevent uncontrolled electrolyte contact of portions of cathode 11 at interface 110 with insulator 15, a pressure seal of the type disclosed in our commonly assigned U.S. Pat. No. 4,096,047 is generally preferred.

In order to thermally protect cell 10 according to the inventive method, an annular confined channel or chamber 121 is provided and a heat conductive layer 120 separates chamber 121 from electrolyte space 13; layer 120 constitutes the electrolyte-exposed surface of the anode 12 and consists of a metal suitable for use as anode, e.g. silver or the like heat conductive and electrically conductive metal suitable for use as an electrode that can be "consumed" by the electrochemical reaction of interest. Preferably, layer 120 is an integral part of anode 12.

Two elongated conduits 124, 122 extend through the body of cell 10 so that a heat transfer medium can be passed through annular chamber 121.

When the sensor face of cell 10 and generally an adjacent portion of jacket 16 is exposed to heat-sterilizing temperatures of typically about 120° C., the electrolyte near the sensor face would be heated through membrane 14 and reach temperatures far outside of the normal operative temperature range of cell 10 with the consequence of damaging its structure or impairing its sensitivity.

According to the method of the invention, a heat exchange is effected within cell 10 by passing heat transfer or coolant fluid, such as air or water, into one conduit 122, 124 through chamber 121 and out through the other conduit; as a consequence, the electrolyte in electrolyte space 13 adjacent to the heat conductive anode portion 120 will be in heat exchange contact with the heat transfer fluid passing through chamber 121.

Heat compensation of the electrolyte in electrolyte space 13 can be controlled simply by adjusting the rate of passage of the heat transfer or coolant medium through chamber 121. Typically, with a convenient coolant such as tap water having tap temperature in the range of from about 5° to 20° C., passage rates of typically between 0.5 and 2.5 milliliters per second will be sufficient for satisfactory heat compensation of the electrolyte during heat-sterilization at 120° C.

The difference between the temperature of the coolant at the inlet and outlet ends of conduits 122, 124 can be used to ascertain that a sufficient passage rate is maintained; typically, that difference should be small, say below 5° C., and passage of coolant will be continued at least as long as heat-sterilization proceeds. Sterilization periods of minutes or hours are conventional in microbiological processes.

It is essential, according to the invention, that the heat exchange explained above should be effected within cell 10, i.e. without cooling any outer parts thereof, intended to be heat-sterilized, to temperatures that are too low for the sterilization effect.

It will be understood that the bottom end of cell 10 and an adjacent portion of jacket 16 are not intended for exposure to heat-sterilization when cell 10 is maintained in-line in an apparatus; as is conventional for sterilizable probes, only its sensor face portion, optionally with an adjacent jacket portion, extending into the processing vessel or line, is in contact with biologically active medium therein; the bottom portion of the cell is maintained outside of the vessel and a seal, coupling or the like will be provided to maintain jacket 16 of cell 10 in sealing engagement with the wall of the processing vessel or line. As such couplings and seals are conventional, this aspect will not be discussed in more detail.

As will be apparent from the diagram of cell 10 in FIG. 1A, the passage of coolant through chamber 121 should not prevent the outer surface of jacket 16 from reaching sterilizing temperatures where sterilization is required. Thus, a thermal insulation of the heat conducting member that is in thermally conducting contact with the coolant, e.g. anode 12, and the outer surface of jacket 16 may be required and is indicated, diagrammatically, in FIG. 1A in that jacket 16 is provided with a relatively thick wall 160 of a thermally insulating material as defined above, e.g. an organic polymer.

However, additional heat insulation of the outermost heat conductive member that is in direct thermal contact with the coolant (anode 12 in FIG. 1A) and an adjacent jacket (16 in FIG. 1A) may be desirable, and a preferred example will be explained below in connection with FIG. 5.

Figure 1B:
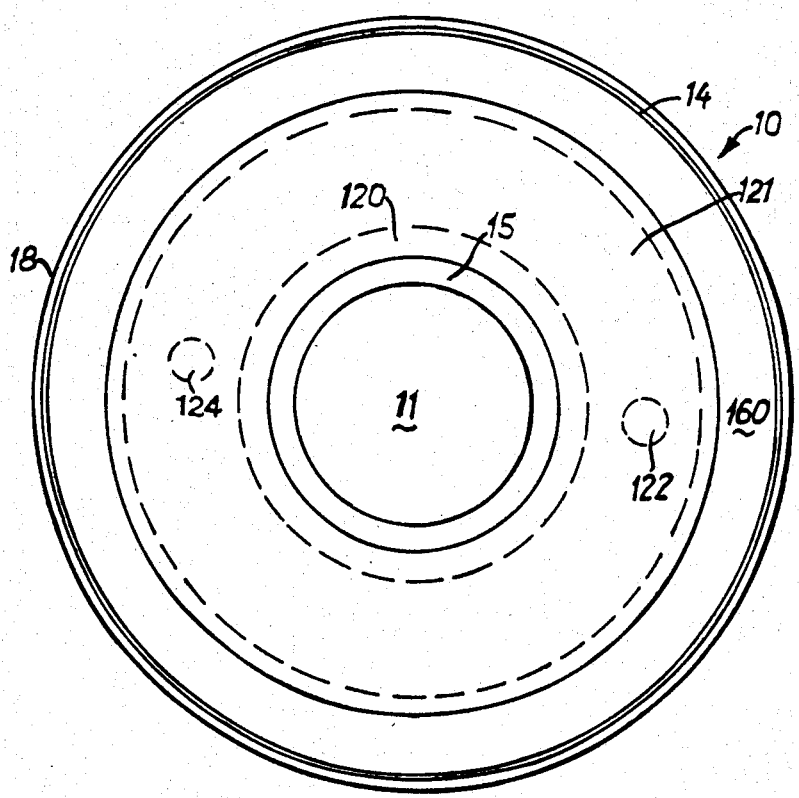
FIG. 1B is the top-view of the cell shown in FIG. 1A.

The top view of cell 10 in FIG. 1B shows the preferred coaxial arrangement of the electrodes 11, 12 and the preferred annular shape of chamber 121 (broken lines) with the ends of conduits 122, 124 (broken lines) in mutual communication through chamber 121.

Figure 2A:
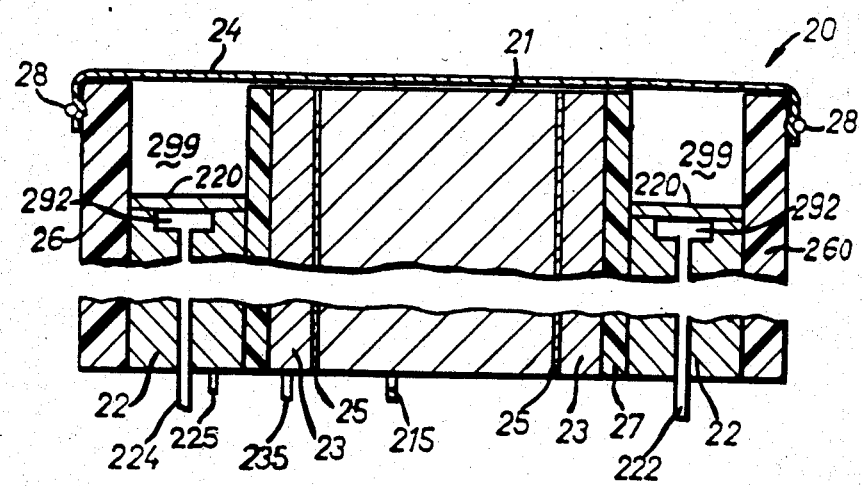
FIG. 2A is a cross-sectional diagrammatic view of a modification of the cell shown in FIGS. 1A, 1B.
Figure 2B:
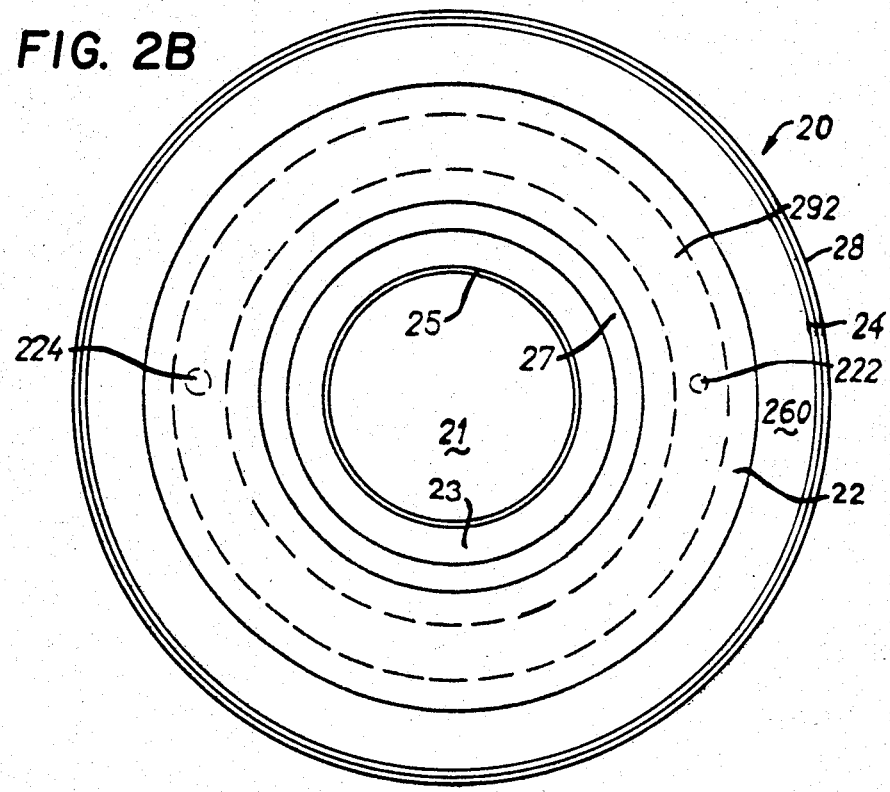
FIG. 2B is a top-view of the cell of FIG. 2A.

Cell 20 shown diagrammatically in FIGS. 2A, 2B illustrates the preferred coaxial electrode arrangement with an additional or guard electrode 23. Advantages and operation of guard electrodes are known per se, e.g. as disclosed in our commonly assigned British Published Patent Application No. 2,013,895, and will not be explained herein.

In order to operate cell 20 of FIGS. 2A, 2B according to the present invention, the outermost or peripheral electrode, i.e. anode 22, of the coaxial electrode structure (comprising cathode 21, guard electrode 23 and anode 22 with electrical insulators 25, 27 between any two adjacent electrodes) is provided with a confined annular channel or chamber 292 separated from electrolyte space 299 by a top wall portion 220 of anode 22. Again, portion 220 may be an integral part of anode 22 or affixed onto the latter but in either case consists of a heat conductive and electrically conductive material, such as silver, to provide for thermal and electrical contact of anode 22 with the electrolyte in electrolyte space 299.

Two conduits 222, 224 extend from the lower end of cell 20 through the cell body and communicate, at their upper ends, through chamber 292. Each electrode is provided with a lead 215, 225, 235 for connection with a conventional measuring instrument (not shown).

For thermal protection of cell 20 when exposed at its sensor face (outer surface of membrane 24 on top of cathode 21) and, optionally, at an adjacent portion of jacket 26 to heat-sterilization, a coolant fluid will be passed from the lower end of cell 20 (maintained outside of vessel in which heat-sterilization is required as explained above) into one of the conduits 222, 224, through annular channel or chamber 292 and out of the other conduit.

It will be noted that heat exchange between the conduits 222, 224 and an adjacent heat conductive tubular member, such as anode 22, of cell 20 may serve to thermally protect the inner cell components (i.e. those encompassed by the heat conductive member) and this is advantageous as explained below if thermal insulation, e.g. insulating wall 260, is provided between that member and the outer surface portion of jacket 26 that is intended to be heat-sterilized.

Again, the top-view shown in FIG. 2B is given to illustrate the coaxial electrode arrangement and the position of annular channel or chamber 292 in the outermost or peripheral electrode (anode 22).

It will be apparent from the explanation of FIGS. 1A, 2A that an indirect heat exchange is effected between the coolant in the separate annular channel or chamber 121, 292 and the electrolyte because of the intermediate heat conductivity of anode wall 120, 220. However, a direct heat exchange is possible when operating the inventive method; in that case, anode wall portion 120, 220 is omitted and electrolyte is circulated as coolant through the conduits but a separate heat exchanger is required for cooling the circulating electrolyte.

Figure 3:
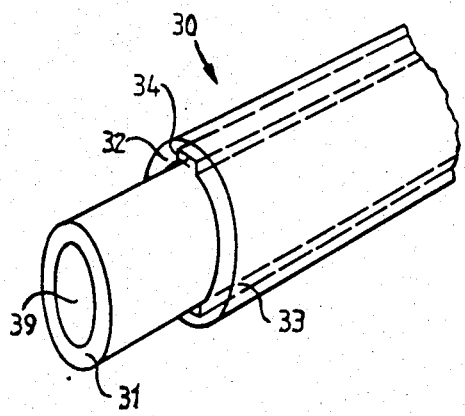
FIG. 3 is a diagrammatic perspective view of a pair of tubular probe members forming fluid-passing channels at their interface in the membrane-enclosed amperometric probe as shown in FIG. 5.
Figure 4:
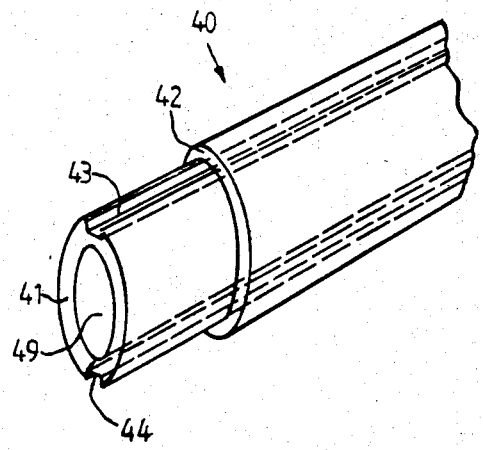
FIG. 4 is a diagrammatic perspective view of a modification of the pair of tubular probe members shown in FIG. 3.

FIGS. 3 and 4 are intended to show, in a semi-diagrammatic perspective view, how the problem of passing a fluid through a MEAC-type probe is solved in a preferred embodiment of the membrane-enclosed amperometric probe according to the invention described hereinbelow with reference to FIGS. 5 and 6.

Pairs 30, 40 of interfitting tubular members 31, 32; 41, 42 are used and a pair of axially extending channels 33, 34; 43, 44 is formed at the interface of each pair 30, 40 by means of grooves or similar elongated recesses that may be formed in the inner surface of the outer tube (32 in FIG. 3), or in the outer surface of the inner tube (41 in FIG. 4), or by a combination thereof (not shown).

For many purposes of the invention it is preferred that one tubular member of the pair is made of a heat conductive material, e.g. a metal such as silver, copper or the like, or metal alloy, while the other member is made of a thermally insulating material such as an organic plastic, e.g. selected from cured epoxides, polypropylene, Nylon 66, polyethylene, terephthalate, acrylics including polymethacrylic esters, polystyrene, polyvinyl chloride (unplasticized), high density polyethylene, polyvinylidene fluoride, polyvinyl carbazole, polyvinyl acetate, polysulfones, polycarbonates including polybisphenol carbonate, polyphenylene oxide, polyurethane, polyacetals including polyoxymethylene and various copolymers including those made of styrene and acrylonitrile or of styrene, acrylonitrile and butadiene.

It will be understood that more than two channels can be provided at the interface of the interfitting tubular members and that the grooves or other types of recesses or channel-forming distancing means could spiral around the interface. Also, fluid-passing channels could be formed between different interfaces of interfitting tubular members as the preferred pairwise arrangement of interfitting tubes for providing channels at one interface is but a preferred embodiment. According to a preferred embodiment of the invention, such a pair of interfitting tubes is used as a thermal shield inside the outer jacket of a probe with a thermally insulating layer, e.g. an air gap, between the probe jacket and the tube pair; in that case, it is preferred for many purposes that the outer member of the pair is made of a heat conducting material, see also FIG. 6.

Figure 6:
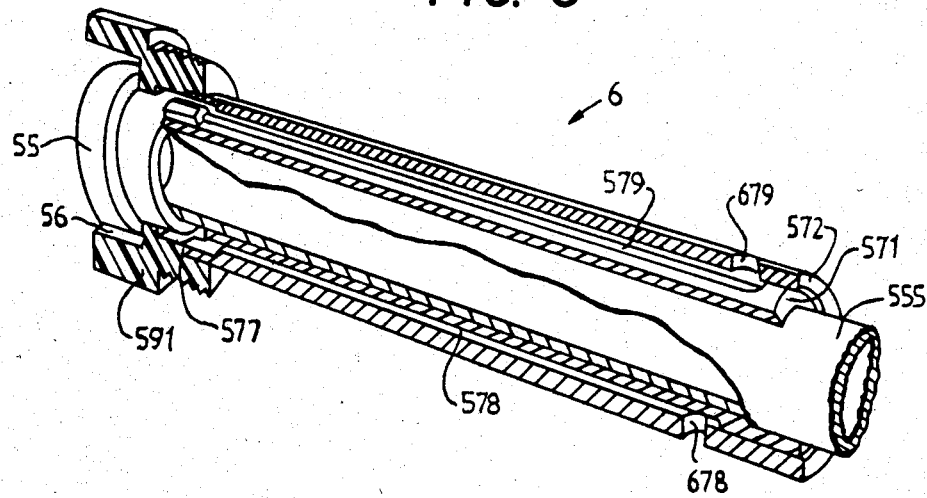
FIG. 6 is a perspective view of the thermal shield constituent of the probe of FIG. 5.
Figure 5:
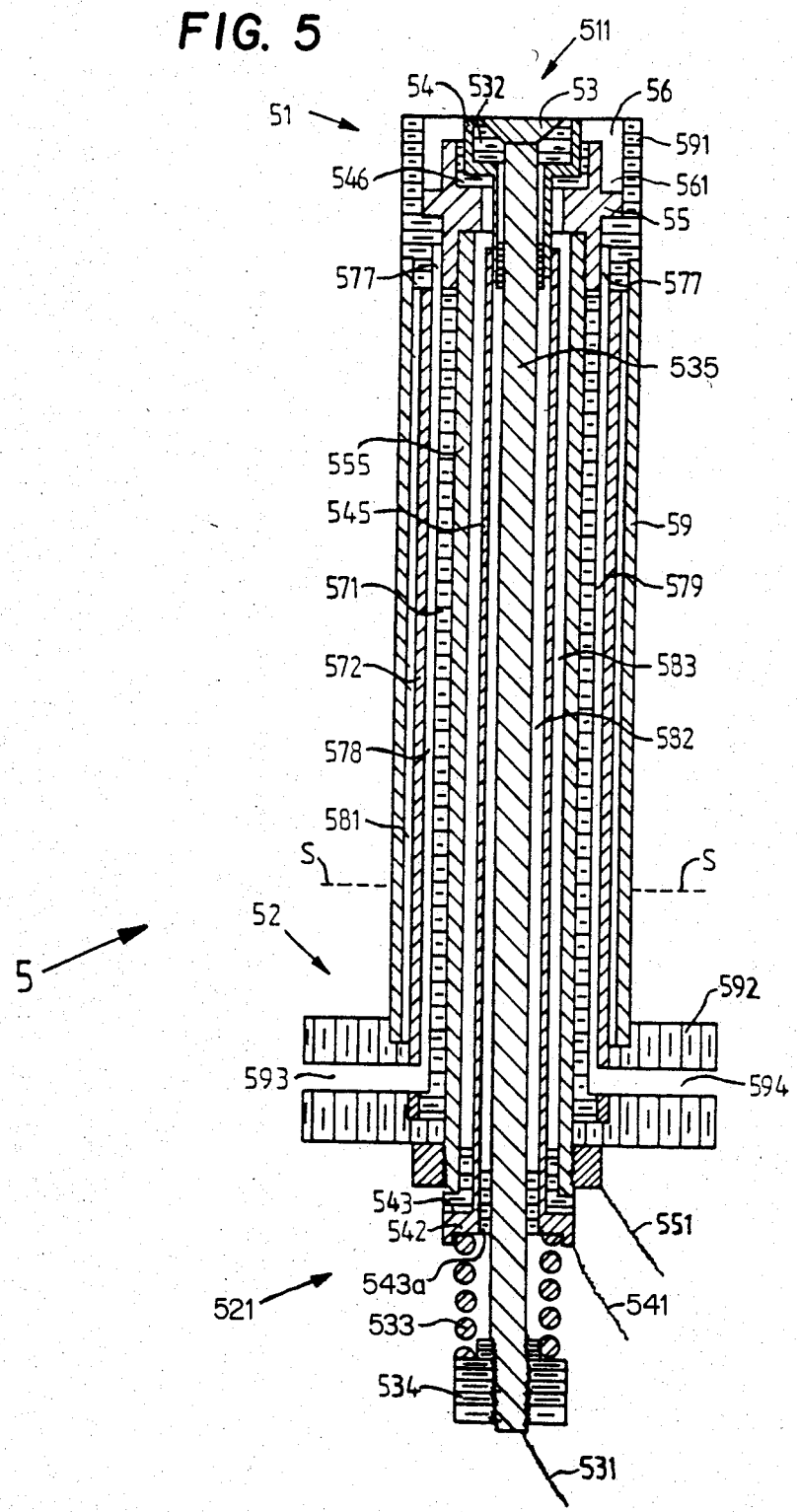
FIG. 5 is a semi-diagrammatic sectional view of a member-enclosed amperometric probe according to the invention.

The channels 33, 34; 43, 44 of such pairs of interfitting tubes will have, or be connected with, mutually communicating ends (not shown in FIGS. 3, 4) in a first cell or probe region near the probe sensor end, e.g. the annular chamber 577 of FIGS. 5, 6 or another type of communicating passage which, in turn, preferably is in heat conducting connection with the electrolyte space.

Further, these channels will have separate fluid-feeding ends (not shown in FIGS. 3, 4), generally with a connection or line for feeding heat exchange fluid, and these fluid-feeding ends will be in a cell or probe region that is distanced from the sensor end and generally is near the other or opposite end of the cell or probe body. By this, it is meant that the communicating ends are in that probe portion which at its outer surface is exposed to temperatures outside the operative range, e.g. to heat-sterilizing conditions, while the fluid-feeding ends of the channels are in a region of the probe body that is not normally subject, at its outer side, to heat-sterilizing conditions. Generally, the "first cell or probe region" is that part of the probe which will be situated within a vessel, line, tank or other processing equipment that requires oxygen monitoring and periodic heat-sterilization; by the same token, the "second region" of the cell or probe is that part of the probe which extends outside of the walls of the processing equipment and is not normally exposed to the heat-sterilization conditions within the equipment.

A preferred embodiment of a membrane-enclosed amperometric probe according to the invention is illustrated in a semi-diagrammatical cross-sectional view in FIG. 5 showing a cell or probe in the form of a cylindrical body 5 having a first probe portion 51 near sensor face 511 and a second probe portion 52 near the opposite probe end 521 where electrical connections or leads 531, 541, 551 are provided for separately connecting the central sensing electrode or cathode 53, the optional intermediate or guard electrode 54 and the peripheral counter electrode or anode 55 with a conventional amperometric measuring device (not shown).

For in-line operation of probe 5 according to the invention, the first probe portion or exposed end 51 of probe 5 will extend into a fermenter, feed-line, tank or the like enclosed equipment (not shown) for microbiological, enzymatic or the like processing requiring periodical heat-sterilization.

For operation, a pressure sealing means (not shown) will be connected with a portion of socket 592 or jacket 59 to ensure sealing connection of probe 5 with an opening of the processing equipment and the second probe portion or external region 52 of probe 5. The first or immersed probe portion 51 includes the electrolyte space 56 having a well or reservoir portion 561 and contacting the sensing electrode 53 by a thin film (not shown) of the electrolyte between the surface of electrode 53 and the semipermeable membrane (not shown). An insulator 532 is in pressure engagement as disclosed in U.S. Pat. No. 4,096,047 with the electrode 53 by means of a spring 533 between nut 534 on the threaded end of cathode-holding rod 535 and the end 542 of tube 545.

Metal tube 545 provides the electrical connection between guard electrode 54 and its connecting lead 541. Metal tube 555 provides for electrical connection between anode 55 and anode lead 551. The metal tubes 545, 555 extend through the cylindrical body 5.

A pair of coaxially arranged interfitting tubular members 571, 572 around anode tube 555 forms a pair of elongated fluid-passing channels 578, 579 by a pair of grooves as explained with reference to FIGS. 3, 4 above and further shown in FIG. 6. Tube 571 is made of an organic polymer, while tube 572 is made of metal. As evident from FIGS. 5 and 6, the fluid-passing channels 578, 579 axially extend through the cylindrical body 5 from the first region of the first probe portion 51 into the second region of the second probe portion 52 and communicate at their ends located in the first region and are connected to fluid-feeding ends located at the second region.

An annular channel or chamber 577 serves to connect the "upper" ends of channels 578, 579 while each lower end of channels 578, 579 is connected with a separate socket bore 593, 594 for feeding a heat transfer fluid into one bore 593, 594 through one channel 578, 579 to the annular channel chamber 577 and out through the other channel 579, 578 and the other bore 594, 593.

The inner wall portion of annular channel or chamber 577 is formed by a portion of anode 55 which consists of a metal, such as silver, which is heat conducting. As anode 55 also contacts electrolyte space 56, controlled heat exchange of the electrolyte in space 56 with the heat transfer fluid passing through annular channel 577 via the heat conducting material of anode 55 can be effected by controlling the passage of heat transfer fluid.

As indicated, one of the interfitting tubular members 571, 572 forming channels 578, 579 at their interface preferably is made of a heat conducting metal, e.g. the outer tubular member 572 in FIG. 5, while the other may be made of an organic polymer.

Because a coolant that passes through channels 578, 579 will have a cooling effect on tube 572, a heat insulation between tube 572 and jacket 59 is provided by means of an annular air gap 581.

The upper end of metal tube 572 bears on jacket head 591 which consists of a material having a low thermal conductivity, such as an organic polymer of the type exemplified above. Jacket 59 (and an optional coat on jacket head 591) consists of a metal, such as stainless steel, but might also consist of an organic polymer of the type illustrated above optionally provided with a metal coating depending upon use requirements including ambient conditions such as temperature and pressure requirements at normal or temporarily abnormal exposures.

For holding the membrane (not shown in FIG. 5) in operative position at the sensor face 511, use of a membrane holding means of the type disclosed in the above mentioned U.S. patent application Ser. No. 164,291, filed June 30, 1980, is preferred for many probe uses; the disclosure of the just mentioned U.S. patent application is incorporated herein by way of reference.

Briefly, such holding means include a substantially non-resilient and creep-resistant ring (not shown in FIG. 5) slidingly fitting onto the membrane-supporting end of jacket 591. A recessed cylindrical end portion (not shown in FIG. 5) of the upper end of jacket 591 may be provided to define the membrane holding position of the ring and a resilient member, e.g. an O-ring, may be provided between the end portion of jacket 591 and the contacting membrane portion.

Further, sealing members, such as O-rings (not shown in FIG. 5), may be provided within the probe body in positions where additional sealing connections are desired, e.g. between mutually contacting ends of electrically insulating and electrically conductive probe members. Line S in FIG. 5 is intended to indicate an external sealing connection with the wall of a fermenter, tube, tank or the like into which the first probe portion or exposed end 51 of the sensor protrudes.

Preferably, at least one temperature sensor, e.g. a thermistor, is arranged within probe 5 (not shown in the drawings) and will have leads for connection with an instrument (not shown). Two, three or more temperature sensors can be arranged within the sensor, e.g. within gap 581, and in a thermally conducting connection with the ambient medium contacting the first probe portion or exposed sensor portion 51.

Preferably, at least one such temperature sensor is used to trigger passage of heat transfer fluid through the probe when the ambient temperature rises above a predetermined temperature, e.g. the upper or lower end of the operative temperature range as explained above. The same temperature sensor or an additional temperature sensor may be used to control the rate of passing heat exchange fluid through the probe in response to variations of the ambient temperature.

Additional annular tubular air gaps 582, 583 may be provided for additional thermal insulation if desired and distancing or closing means 543, 543a may be inserted for gap definition.

FIG. 6 is a simplified, partially sectioned perspective view of the thermal shield 6 formed by the interfitting pair of tubular members 571, 572 of FIG. 5 with channels 578, 579 at their interface. Thermal shield 6 is shown to contact the anode connecting tube 555 but this is not believed to be critical.

The separate fluid-feeding ends of channels 578, 579 are defined by bores 678, 679 in metal tube 572 while communication of the opposite (i.e. near sensor face) ends is established by annular channel 577 extending around the body of anode 55. Thus, heat exchange of the heat transfer fluid in channel 577 through the thermally conducting metal of the peripheral anode with the electrolyte in space 56 is maintained and a thermal shield extending through the probe in all its portions where undesirable temperature impact should be prevented is provided within the probe body without impairing sterilization at the outer probe surface because of the thermal insulation between the shield and the jacket as explained above.

EXAMPLE

The following non-limiting example of working the method according to the invention is given for illustration of thermal MEAC protection during heat sterilization.

The electrolyte space of a sensor similar in its essential features to that illustrated in FIG. 5 was filled with an alkaline potassium chloride electrolyte and enclosed by a 0.1 mm thick polytetrafluoroethylene membrane. Its sensitivity towards oxygen dissolved in water was determined to be 0.485 microamperes per ppm dissolved oxygen by exposing it to flowing air-saturated water thermostated at 25° C.

It was then sealed into a pressure vessel together with sufficient water to maintain a water vapor saturated atmosphere in the vessel at 120° C. The sensing face 511 and part of the cylindrical probe body adjoining this face were enclosed within the pressure vessel and the cooling fluid inlet and outlet bores 593 and 594 were accessible outside the vessel. Tap water was passed through the cooling channels to act as heat exchange medium at the rate of 15 liters per hour.

The pressure vessel was heated during 2 hours on an electrically heated hot plate at a temperature of 120° C. The total pressure in the vessel at this temperature was 4 bars, of which 2 bars were due to the partial pressure of water vapor. A temperature rise of only 2° C. was measured between the inlet and outlet of the stream of cooling water. After this treatment the pressure vessel was suddenly opened to permit escape of the steam and cooled rapidly under fast running water thereby subjecting the sensor to extremely abrupt changes of ambient pressure and temperature. This treatment is believed to be the harshest that the sensor might ever be expected to withstand in the course of heat sterilization and would be sufficient to blow the membrane off a sensor which did not benefit from the protection of the heat compensation feature.

No visible effects on the sensor were observable as a consequence of the described sterilization treatment. The sensitivity of the sensor was redetermined in the same fashion as prior to sterilization. A sensitivity of 0.480 microamperes per ppm was found revealing a downward drift of only 1.1% as a result of the sterilization.

The sensor was further shown to be capable of withstanding a series of repeated treatments of the same type without harm.

It will be appreciated that the provision of fluid channels extending through an essential portion of a probe body by means of a pair of interfitting tubular members with a grooved interface as disclosed herein can be of use for purposes other than thermal protection, e.g. for circulation or regeneration of electrolyte in special applications of MEAC-type probes.

Further, while thermal protection of MEAC-type probes is of particular importance for in-line use of probes in an apparatus that requires periodical heat-sterilization, other types of probe operation that include exposure of the probe sensor face to temperatures above or below the operative temperature range can be envisaged so that heat protection of MEACs by the inventive method and a heat-sterilizable probe are preferred but non-limiting examples of the utility of the present invention.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What we claim is:

1. In a membrane-enclosed amperometric probe comprising an elongated and generally cylindrical body having a sensor face at one end of said body; an electrolyte space covered by said membrane and in contact with at least two electrodes; an electrical connecting means extending from said electrodes through said body to a region near the other end of said body; the improvement which comprises said body comprising at least two elongated fluid-passing conduits not being in fluid communication with said electrolyte space and extending in axial direction through said body from a first region near said one end of said body to a second region near said other end of said body; said conduits having mutually communicating ends in said first region and separate fluid-feeding ends in said second region.

2. In a membrane-enclosed amperometric probe comprising an elongated and generally cylindrical body having a sensor face at one end of said body; an electrolyte space covered by said membrane and in contact with at least two electrodes; and electrical connecting means extending from said electrodes through said body to a region near the other end of said body; the improvement which comprises said body comprising at least two elongated fluid-passing conduits extending in axial direction through said body from a first region near said one end of said body to a second region near said other end of said body; said conduits having mutually communicating ends in said first region and separate fluid-feeding ends in said second region; and said conduits being in heat-conductive connection but not in fluid communication with said electrolyte space at their mutually communicating ends in said first region near said one end of said body.

3. In a membrane-enclosed amperometric probe comprising an elongated and generally cylindrical body having a sensor face at one end of said body; an electrolyte space covered by said membrane and in contact with at least two electrodes; an electrical connecting means extending from said electrodes through said body to a region near the other end of said body; the improvement which comprises said body comprising at least two elongated fluid-passing conduits not being in fluid communication with said electrolyte space and extending in axial direction through said body from a first region near said one end of said body to a second region near said other end of said body; said conduits having mutually communicating ends in said first region and separate fluid-feeding ends in said second region; and said mutually communicating ends being in heat-exchange contact with a heat conducting cell member which, in turn, is in heat exchange contact with said electrolyte space.

4. In a membrane-enclosed amperometric probe comprising an elongated and generally cylindrical body having a sensor face at one end of said body; an electrolyte space covered by said membrane and in contact with at least two electrodes; and electrical connecting means extending from said electrodes through said body to a region near the other end of said body; the improvement which comprises said body comprising at least two elongated fluid-passing conduits not being in fluid communication with said electrolyte space and extending in axial direction through said body from a first region near said one end of said body to a second region near said other end of said body; said conduits having mutually communicating ends in said first region and separate fluid-feeding ends in said second region; and said mutually communicating ends opening into a substantially annular confined channel sealed from said electrolyte space but maintained in heat-exchange contact therewith by a heat-conducting cell member.

* * * * *